United States Patent [19]

Mayer et al.

[11] Patent Number: 5,321,012

[45] Date of Patent: Jun. 14, 1994

[54] INHIBITING THE DEVELOPMENT OF TOLERANCE TO AND/OR DEPENDENCE ON A NARCOTIC ADDICTIVE SUBSTANCE

[75] Inventors: David J. Mayer; Donald D. Price; Jianren Mao, all of Richmond, Va.; John W. Lyle, Belmar, N.J.

[73] Assignee: Virginia Commonwealth University Medical College, Richmond, Va.

[21] Appl. No.: 43,280

[22] Filed: Apr. 6, 1993

Related U.S. Application Data

[63] Continuation-in-part of Ser. No. 10,583, Jan. 28, 1993, abandoned.

[51] Int. Cl.⁵ .................. A61K 31/70; A61K 31/55; A61K 31/54; A61K 31/44
[52] U.S. Cl. ...................... 514/25; 514/216; 514/223.5; 514/225.5; 514/224.5; 514/282; 514/231.2; 514/289; 514/812; 536/53; 536/55.1
[58] Field of Search ............ 514/25, 282, 812, 223.5, 514/225.5, 224.5, 216; 536/53, 55.1

[56] References Cited

U.S. PATENT DOCUMENTS

| | | | |
|---|---|---|---|
| 2,770,569 | 11/1956 | Fromherz et al. | 167/65 |
| 4,126,684 | 11/1978 | Robson et al. | 424/254 |
| 4,316,888 | 2/1982 | Nelson | 424/127 |
| 4,362,870 | 12/1982 | Portoghese | 542/403 |
| 4,416,871 | 11/1983 | Walter et al. | 424/177 |
| 4,446,140 | 5/1984 | Nelson | 424/260 |
| 4,464,378 | 8/1984 | Hussain | 424/260 |
| 4,476,141 | 10/1984 | Cormier | 424/321 |
| 4,758,559 | 7/1988 | Wasley et al. | 514/211 |
| 4,788,055 | 11/1988 | Fischer et al. | 424/79 |
| 4,806,543 | 2/1989 | Choi | 514/464 |
| 4,816,264 | 5/1989 | Phillips et al. | 424/468 |
| 4,816,450 | 3/1989 | Bell et al. | 514/25 |
| 4,828,836 | 5/1989 | Elger et al. | 424/464 |
| 4,834,965 | 5/1989 | Martani et al. | 424/488 |
| 4,834,985 | 5/1989 | Eiger et al. | 424/488 |
| 4,888,347 | 12/1989 | Woodruff et al. | 514/289 |
| 4,906,779 | 5/1990 | Weber et al. | 564/238 |
| 4,912,114 | 3/1990 | Revesz | 514/282 |
| 4,919,916 | 4/1990 | Golwyn | 424/10 |
| 4,924,008 | 5/1990 | Abou-Gharbia et al. | 514/812 |
| 4,937,232 | 6/1990 | Bell et al. | 514/26 |
| 4,942,182 | 7/1990 | Weiss et al. | 514/812 |
| 4,959,493 | 9/1990 | Ohfume et al. | 562/506 |
| 4,975,430 | 12/1990 | Jahr et al. | 514/255 |
| 4,990,519 | 2/1991 | Jones et al. | 514/314 |
| 4,994,446 | 2/1991 | Sokolovsky et al. | 514/75 |
| 4,994,467 | 2/1991 | Zimmerman | 514/284 |
| 4,996,047 | 2/1991 | Kelleher et al. | 424/79 |
| 5,013,540 | 5/1991 | Redburn | 424/10 |
| 5,028,611 | 7/1991 | Halikas | 514/277 |
| 5,028,707 | 7/1991 | Nichols et al. | 546/156 |
| 5,034,395 | 7/1991 | Tamada et al. | 514/277 |
| 5,034,400 | 7/1991 | Olney | 514/315 |
| 5,041,446 | 8/1991 | Silvestrini | 514/255 |
| 5,047,229 | 9/1991 | Nahas et al. | 424/10 |

(List continued on next page.)

OTHER PUBLICATIONS

Koyunchoglu et al., *International Journal of Clinical Pharmacology, Therapy and Toxicology*, vol. 28, No. 4 1990 (147-152), The treatment of heroin addicts with dextromethorphan: A double-bine comparison of dextromethorphan with chlorpromazine.

Marek et al. Abstract No. 92034071, *Brain-Res.*, Aug. 30, 1991 558(1). pp. 163-165.

(List continued on next page.)

*Primary Examiner*—Frederick E. Waddell
*Assistant Examiner*—T. J. Criares
*Attorney, Agent, or Firm*—Dilworth & Barrese

[57] ABSTRACT

Nontoxic substances that block the N-methyl-D-aspartate (NMDA) receptor, e.g., a morphinan such as dextromethorphan or dextrorphan, or that block a major intracellular consequence of NMDA receptor activation, e.g., a ganglioside such as $GM_1$ or $GT_{1b}$, a phenothiazine such as trifluoperazine or a naphthalenesulfonamide such as N-(6-aminohexyl)-5-chloro-1-naphthalenesulfonamide, inhibit the development of tolerance to and/or dependence on addictive drugs, e.g., narcotic analgesics such as morphine, codeine, etc.

9 Claims, 10 Drawing Sheets

U.S. PATENT DOCUMENTS

| | | | |
|---|---|---|---|
| 5,051,426 | 9/1991 | Parnell | 514/263 |
| 5,051,442 | 9/1991 | Salituro et al. | 514/419 |
| 5,057,519 | 10/1991 | Suberg | 514/282 |
| 5,071,646 | 12/1991 | Malkowska et al. | 424/497 |
| 5,075,341 | 12/1991 | Mendelson et al. | 514/282 |
| 5,091,391 | 2/1992 | Aizenman et al. | 514/311 |
| 5,093,129 | 3/1992 | Horivitz et al. | 424/451 |
| 5,093,525 | 3/1992 | Weber et al. | 564/238 |
| 5,095,009 | 3/1992 | Whitten et al. | 514/85 |
| 5,106,847 | 4/1992 | Salituro et al. | 514/232.5 |
| 5,109,017 | 4/1992 | Schmesing et al. | 549/77 |
| 5,118,675 | 6/1992 | Jirkovsky et al. | 514/80 |
| 5,124,319 | 6/1992 | Baudy et al. | 514/80 |
| 5,124,340 | 6/1992 | Jaffe et al. | 514/279 |
| 5,133,974 | 7/1992 | Paradissis et al. | 424/480 |
| 5,137,889 | 8/1992 | Tamada et al. | 514/252 |
| 5,137,919 | 8/1992 | Igarashi et al. | 564/642 |
| 5,141,957 | 8/1992 | Jiang et al. | 514/510 |
| 5,145,842 | 9/1992 | Driedger et al. | 514/63 |
| 5,151,360 | 9/1992 | Handa et al. | 435/240.2 |
| 5,171,752 | 12/1992 | Caldirola et al. | 514/648 |
| 5,183,807 | 2/1993 | della Valle et al. | 514/25 |
| 5,185,329 | 2/1993 | Gawin et al. | 514/159 |
| 5,190,925 | 3/1993 | della Valle et al. | 514/25 |

OTHER PUBLICATIONS

Marek et al. Abstract No. 91316632, *Brain-Res.*, Apr. 26, 1991 547(1). pp. 77–81.

Tanganelli et al. Abstract No. 91226742, *Neurosci-Lett.*, Jan. 28, 1991 122(2). pp. 270–272.

Trujillo et al. Abstract No. 91095981, *Science*, Jan. 4, 1991 251(4989). pp. 85–87.

INHIBITING THE DEVELOPMENT OF TOLERANCE TO AND/OR DEPENDENCE ON A NARCOTIC ADDICTIVE SUBSTANCE

CROSS REFERENCE TO RELATED APPLICATION

This application is a continuation-in-part of copending U.S. patent application Ser. No. 08/010,583, filed Jan. 28, 1993, now abandoned.

BACKGROUND OF THE INVENTION

This invention relates to a composition containing an addictive substance and a component which inhibits the development of tolerance to and/or dependence on the addictive substance. More particularly, the invention relates to a composition containing an addictive substance such as morphine or codeine and at least one nontoxic substance that blocks the N-methyl-D-aspartate (NMDA) receptor, e.g., a morphinan such as dextromethorphan or dextrorphan, or that blocks at least one major intracellular consequence of NMDA receptor activation, e.g., a ganglioside such as ganglioside $GM_1$ or $GT_{1b}$, a phenothiazine such as trifluoperazine or a naphthalenesulfonamide such as N-(6-aminohexyl)-5-chloro-1-naphthalenesulfonamide.

Morphine is a rapid and effective drug for the treatment of severe pain but its long term administration has been limited due to its negative side effects, principally tolerance and dependence, which develop rapidly after administration. In an effort to make morphine of greater use in the treatment of pain, it has been combined with a variety of substances intended to inhibit one or more of its undesirable side effects. U.S. Pat. No. 2,770,569 describes the combination of morphine with the compound levo-d-hydroxy-N-allyl-morphinan which is said to suppress or eliminate such undesirable side reactions of morphine as depression, nausea and vomiting. U.S. Pat. No. 4,126,684 discloses reducing either the addiction liability of an addictive substance such as a narcotic analgesic or a barbiturate or the withdrawal symptoms caused by deprivation of such a substance in an addicted subject by administering the addictive substance, e.g., morphine, with a 4-amino-3-p-halophenylbutyric acid. U.S. Pat. No. 4,415,871 describes the prevention of treatment tolerance and physical dependence in chronic morphine treatment by combining the morphine with any of the specific dipeptides indicated therein. U.S. Pat. No. 5,041,446 discloses inhibiting the development of tolerance to morphine by combining the morphine with dapiprazole. U.S. Pat. No. 5,057,519 achieves a reduction in morphine tolerance by combining the morphine with a benzamide antagonist for a subtype of the serotonin receptor, 5-HT$_3$. Trujillo et al., "Inhibition of morphine tolerance and dependence by the NMDA receptor antagonist MK-801", *Science*, 251 (4989), pp. 85-87, Jan. 4, 1991; Tanganelli et al., "Glutamate antagonists prevent morphine withdrawal in mice and guinea pigs", *Neuroscience Letters*, 122(2), pp. 270-272, Jan. 28, 1991; Marek et al., "Excitatory amino acid antagonists (kynurenic acid and MK-801) attenuate the development of morphine tolerance in the rat", *Brain Research*, 547(1), pp. 77-81, Apr. 26, 1991; and, Marek et al., "Delayed application of MK-801 attenuates development of morphine tolerance in rats, *Brain Research*, 558(1), pp. 163-165, Aug. 30, 1991 discuss the role of MK-801 (the compound 5-methyl-10,11-dihydro-SH-dibenzo[a,d]cyclohepten-5,10-imine), an NMDA receptor antagonist or blocker, in reducing morphine dependence in laboratory animals. However, MK-801 has been found to be toxic and is therefore unsuitable for pharmaceutical use.

SUMMARY OF THE INVENTION

In accordance with the present invention, a composition is provided which comprises an addictive substance and at least one nontoxic substance that blocks the N-methyl-D-aspartate receptor or at least one major intracellular consequence of N-methyl-D-aspartate receptor activation.

Further in accordance with the present invention, a method of inhibiting the development of tolerance to and/or dependence on an addictive substance administered to a mammal which is liable to addiction thereto is provided which comprises administering the addictive substance to the mammal before, with or following administration to the mammal of a tolerance-reducing and/or dependence-reducing amount of at least one nontoxic substance that blocks the N-methyl-D-aspartate receptor or at least one major intracellular consequence of N-methyl-D-aspartate receptor activation.

Still further in accordance with this invention, a method of alleviating withdrawal symptoms in a mammal addicted to an addictive substance is provided which comprises administering to the addicted mammal the addictive substance before, with or following administration to the mammal of a dependence-reducing amount of at least one nontoxic substance that blocks the N-methyl-D-aspartate receptor or the intracellular consequences of N-methyl-D-aspartate receptor activation thereby alleviating withdrawal symptoms when the addictive substance is withdrawn from the mammal.

The term "nontoxic" as used herein shall be understood in a relative sense and is intended to designate any substance that has been approved by the United States Food and Drug Administration ("FDA") for administration to humans or, in keeping with established criteria, is susceptible to approval by the FDA for administration to humans.

BRIEF DESCRIPTION OF THE DRAWINGS:

FIGS. 1–10 are graphical representations of experimental data demonstrating the effectiveness of specific nontoxic substances that block the N-methyl-D-aspartate receptor or a major consequence of N-methyl-D-aspartate receptor activation for inhibiting morphine tolerance and dependence in rats.

DESCRIPTION OF THE PREFERRED EMBODIMENTS

A particularly important category of addictive substances with which the present invention is concerned are the narcotic analgesics, e.g., opiates, opiate derivatives, opioids and their pharmaceutically acceptable salts. Specific examples of narcotic analgesics include alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine and pharmaceutically acceptable salts thereof. For a detailed discussion of these and other narcotic analgesics, reference may be made to Jaffe et al., "Opioid Analgesics and Antagonists" in "Goodman and Gillman's Pharmacological Basis of Therapeutics", Goodman et al., eds. 7th ed., 1985, MacMillan and Company, New York pp. 491-531.

Other addictive substances that can be utilized herein include acetorphine, acetyldihydrocodeine, acetylmethadol, allylprodine, alphracetylmethadol, alphameprodine, alphamethadol, benzethidine, benzylmorphine, betacetylmethadol, betameprodine, betamethadol, betaprodine, clonitazene, cocaine, codeine methylbromide, codeine-N-oxide, cyprenorphine, desomorphine, dextromoramide, diampromide, diethylthiambutene, dihydromorphine, dimenoxadol, dimepheptanol, dimethylthiamubutene, dioxaphetyl butyrate, dipipanone, drotebanol, ethanol, ethylmethylthiambutene, etonitazene, etorphine, etoxeridine, furethidine, hydromorphinol, hydroxypethidine, ketobemidone, levomoramide, levophenacylmorphan, methyldesorphine, methyldihydromorphine, morpheridine, morphine methylpromide, morphine methylsulfonate, morphine-N-oxide, myrophin, nicocodeine, nicomorphine, nicotine, noracymethadol, norlevorphanol, normethadone, normorphine, norpipanone, phenadoxone, phenampromide, phenomorphan, phenoperidine, piritramide, pholcodine, proheptazoine, properidine, propiran, racemoramide, thebacon, trimeperidine and the pharmaceutically acceptable salts thereof.

Still other addictive substances that can be utilized in the practice of the invention include the sedatives and hypnotics, e.g., benzodiazepines such as chlordiazepoxide, clorazepate, diazepam, flurazepam, halazepam, ketazolam, borazepam, oxazepam, prazepam, temazepam, triazolam and the pharmaceutically acceptable salts thereof, barbiturates such as amobarbital, ambobarbital, barbital, butabartital, mephobarbital, methohexital, pentobarbital, phenobarbital, secobarbital, talbutal, thiamylal and thiopental and the pharmaceutically acceptable salts thereof and other sedatives and hypnotics such as chloral hydrate, meprobamate, methaqualone, methyprylon and the pharmaceutically acceptable salts thereof.

By way of inhibiting the development of tolerance to and/or dependence on any of the foregoing and similarly addictive substances, the addictive substance is administered before, with or following the administration of at least one nontoxic substance that blocks the N-methyl-D-aspartate (NMDA) receptor or the intracellular consequences of N-methyl-D-aspartate receptor activation. Activation of the NMDA receptor, a subtype of excitatory amino acid receptors, induces a number of changes in the functional activity of nerve cells, and in particular, their capacity for excitability or inhibition in the presence of an addictive substance, via an increase in intracellular $Ca++$ concentration. The major consequences of NMDA receptor activation include the following sequences, or cascades, of events occurring within nerve cells:

a) translocation and activation of protein kinases such as protein kinase C→ phosphorylation of substrate proteins such as cytosolic enzymes, channel proteins, receptor proteins, etc.→changes in functional activity;

b) initiation of early gene (c-fos, c-jun, zif-268, etc.) expression by either increased intracellular $Ca++$ or $Ca++$-activated protein kinases→expression of functional genes responsible for production of cellular enzymes (such as protein kinases), receptor proteins (such as the NMDA receptor), ion channel proteins (such as $K+$, $Na+$, $Ca++$ channels), neuropeptides (such as dynorphin), etc.→changes in functional activity;

c) $Ca++$/calmodulin (or other $Ca++$ binding proteins) induced activation of enzymes and other cellular components→activation of $Ca++$/calmodulin-protein kinase systems such as $Ca++$/calmodulin kinase II→autophosphorylation of enzymes (e.g., $Ca++$/calmodulin kinase II) or other functional proteins→changes in functional activity;

d) $Ca++$/calmodulin induced activation of constitutive nitric oxide synthase as well as induction of inducible nitric oxide synthase→production of nitric oxide→ i) production of cyclic guanosine monophosphate via activation of guanosine cyclase resulting in activation of protein kinases and early gene expression; ii) direct protein modification such as enzymes, receptor and/or channel proteins; iii) lipid membrane modification and/or nucleic acid modification via scavenge of free radicals; iv) induction of neurotoxicity at higher nitric oxide levels; v) retrograde actions in adjacent neurons or glial cells such as facilitation of glutamate release/NMDA receptor activation and/or inhibition of post-synaptic NMDA receptors→ changes in functional activity;

e) interactions with the cyclic adenosine monophosphate/protein kinase A system, the phospholipase C-inositol triphosphate-$Ca++$/diacylglycerol-protein kinase system, the phospholipase A2-arachidonic acid/-prostanoids/leukotrienes system→changes in functional activity induced by second messenger systems other than NMDA receptor/$Ca++$/$Ca+$-calmodulin/protein kinase systems; and, f) interactions with other excitatory amino acid receptor subtypes including non-NMDA receptors and metabotropic receptors as well as intracellular events subsequent to the activation of these excitatory amino acid receptor subtypes→changes in functional activity induced by the non-NMDA and metabotropic receptor activation.

A substance that blocks the NMDA receptor will effectively prevent all of the foregoing major intracellular sequences of events from taking place. However, even with activation of the NMDA receptor, it is still possible to inhibit the development of tolerance to and/or dependence on an addictive substance by combining the addictive substance with a substance that blocks at least one of the foregoing major intracellular sequences of events. Thus, e.g., a substance that interferes with translocation and activation of protein kinase C or with calmodulin induced activation of constitutive nitric oxide synthase as well as induction of inducible nitric oxide synthase is also useful for the practice of this invention.

Among the nontoxic substances that block the NMDA receptor and as such are useful in the practice of the present invention are morphinans such as dextromethorphan ((+)-3-hydroxy-N-methylmorphinan) and dextrorphan ((+)-3-hydroxy-N-methylmorphinan), their mixtures and the pharmaceutically acceptable salts thereof. Other useful nontoxic substances that block the NMDA receptor include ketamine (2-(2-chlorophenyl)-2-(methylamino)cyclohexanone), pyrroloquinoline quinone and cis-4-(phosphonomethyl)-2piperidinecarboxylic acid.

Nontoxic substances that block a major intracellular consequence of NMDA receptor activation and are therefore useful in the practice of the invention include inhibitors of protein kinase C such as the gangliosides, in particular, ganglioside $GM_1$ (monosialoganglioside) and ganglioside $GT_{1b}$ (trisialoganglioside); amphipathic long chain bases such as sphingosine, N,N,N-trimethylsphingosine, sphinganine and psychosine; quinolyloxazole-2-ones such as 4-methyl-5-(3-quinolinyl)-2-(3H)-oxazolone and phenyl-5-(2-quinolinyl)-2-3(3H)-oxazolone; 1,4-bis-(amino-hydroxyalkylamino)anthraquinones such as 1,4-bis-(3-propylamino-2-hydroxypropylamino)-9,10 anthracenedione and 1,4-bis-(3-benzylamino-2-hydroxypropylamino)-9,10 anthracendione; and, mixtures and pharmaceutically acceptable salts of any of the foregoing.

Additional nontoxic substances that block a major intracellular consequence of NMDA receptor activation and as such are useful in the practice of the invention include inhibitors of calmodulin such as the phenothiazines, in particular, chlorpromazine, chlorpromazine sulfoxide, prochlorperazine dimaleate, perphenazine, trifluoperazine, fluphenazine, fluphenazine enanthate, fluphenazine decanoate, thioridazine, mesoridazine besylate, piperacetazine, acetophenazine dimaleate, carphenazine dimaleate, butaperazine dimaleate and phenothiazine sulfoxide; naphthalenesulfonamides such as N-(6-aminohexyl)-5-chloro-1-naphthalenesulfonamide, N-(6-aminohexyl)-5-chloro-2-naphthalenesulfonamide and N-(6-aminohexyl)-5-bromo-2-naphthalenesulfonamide; 4-substituted-4H,6H-pyrrolo[1,2-a][4,1] benzoxazepines such as 1,3-dihydro-1-(1-[(4-methyl-4H,6H-pyrrolo[1,2-a][4,1] benzoxazepin-4-yl)methyl]-4-piperidinyl)-2H-benzimidazol-2-one; benzhydryls such as N-[2](diphenylmethylthioehtyl]-2-(trifluoromethyl)-benzeneethanamine, N-[2-(bis(4-fluorophenyl)methylthio)ethyl]-2-(trifluoromethyl)benzeneethanamine and N-[2-(bis(4-fluorophenyl)methylthio)ethyl]-3-(trifluoromethyl)benzeneethanamine; tricyclic antidepressant drugs such as imipramine, 2-chloroimipramine and amitriptyline; penfluridol; haloperidol; pimozide; clozapine; calmidazolin; and, mixtures and pharmaceutically acceptable salts of any of the foregoing.

Administration of the composition of this invention can be in the form of a single dosage unit containing both the addictive substance and the nontoxic substance that blocks the NMDA receptor or a major intracellular consequence of NMDA receptor activation or the two substances can be administered separately provided both are ultimately present in effective amounts in the patient. Introduction of the composition into the patient can be by way of oral administration or by intravenous, intramuscular, subcutaneous, intrathecal, epidural or intracerebroventrilcular injection.

The preferred dosage of addictive substance and the nontoxic substance that blocks the NMDA receptor or a major intracellular consequence of NMDA receptor activation can vary widely, e.g., from about 0.25 to about 250 mg/day, but actual amounts will vary according to the particular active substances being used, the particular formulation containing the active substances and the state and circumstances of the host being treated. As those skilled in the art recognize, many factors that modify the action of the active substances herein will be taken into account by the treating physician such as the age, body weight, sex, diet and condition of the subject, the time of administration, the rate and route of administration, and so forth. Optimal dosages for a given set of conditions can be ascertained by those skilled in the art using conventional dosage determination tests in view of the experimental data provided herein.

In alleviating withdrawal symptoms in addicted subjects deprived of the addictive substance, the substance that blocks the NMDA receptor or a major intracellular consequence of NMDA receptor activation can be administered to the subject, together with the addictive substance, at a dosage rate of about 0.25 to about 250 mg/day, again, specific dosage levels and routes of administration being selected in accordance with the subject's circumstances. As a result of this treatment, the subject will experience a reduced level of dependence on the addictive substance eventually reaching the point where total withdrawal of the substance will result in at most mild withdrawal symptoms.

The composition herein can be formulated as a liquid, powder, elixir, injectable solution, etc. Formulations for oral use can be provided as hard gelatin capsules wherein the composition is mixed with an inert solid diluent such as calcium carbonate, calcium phosphate or kaolin, or as soft gelatin capsules wherein the composition is mixed with an oleaginous medium, e.g., liquid paraffin or olive oil.

Aqueous suspensions can contain the composition in admixture with pharmaceutically acceptable excipients such as suspending agents, e.g., sodium carboxymethyl cellulose, methylcellulose, hydroxypropylmethylcellulose, sodium alginate, polyvinylpyrrolidone, gum tragacanth and gum acacia; dispersing or wetting agents such as naturally occurring phosphatide, e.g., lecithin, or condensation products of an alkylene oxide with fatty acids, e.g., polyoxyethylene stearate, or condensation products of ethylene oxide with long chain aliphatic alcohols, e.g, heptadecaethyleneoxycetanol, or condensation products of ethylene exide with partial esters derived from fatty acids and a hexitol, e.g., polyoxyethylene sorbitol monoleate or condensation products of ethylene oxide with partial esters derived from fatty acids and hexitol anhydrides, e.g., polyoxyethylene sorbitan monooleate. Such aqueous suspensions can also contain one or more preservatives, e.g., ethyl- or n-propyl-p-hydroxy benzoate, one or more coloring agents, one or more flavoring agents and one or more sweetening agents, such as sucrose, saccharin or sodium or calcium cyclamate.

Dispersible powders and granules suitable for preparation of an aqueous suspension by the addition of water provide the composition in admixture with a dispersing or wetting agent, suspending agent and one or more preservatives. Suitable dispersing or wetting agents and suspending agents are exemplified by those already mentioned above. Additional excipients, e.g., sweetening, flavoring and coloring agents, can also be present. Syrups and elixirs can be formulated with sweetening agents, for example glycerol, sorbitol or sucrose. Such formulations can also contain a demulcent, a preservative and flavoring and coloring agents.

The composition of this invention or either of its principal active ingredients can be provided in sustained release dosage form of which many kinds are known, e.g., as described in U.S. Pat. Nos. 4,788,055; 4,816,264; 4,828,836; 4,834,965; 4,834,985; 4,996,047; 5,071,646; and, 5,133,974, the contents of which are incorporated by reference herein.

The examples that follow are illustrative of the invention.

EXAMPLE 1

The effect of systemic dextrorphan on prevention of the development of morphine tolerance and dependence was examined in Sprague-Dawley rats weighing 350-400 gm. Morphine tolerance was developed in the rats by twice daily subcutaneous injection of 10 mg/kg morphine sulfate. The analgesic effect of the morphine was examined by using the well known tail-flick test which measures the latency of tail-flick upon radiant heat stimulation. The latency of tail-flick test is defined as the time elapsed from the onset of radiant heat to the flick of the rat's tail. In order to examine the effect of dextrorphan on the development of morphine tolerance, each morphine-treated rat also received intraperitoneal administration of either dextrorphan (1.56, 3.13, 6.25, 12.5 mg/kg, n=5/group) or saline (n=6) given 30 minutes prior to each morphine administration.

Figure 1:
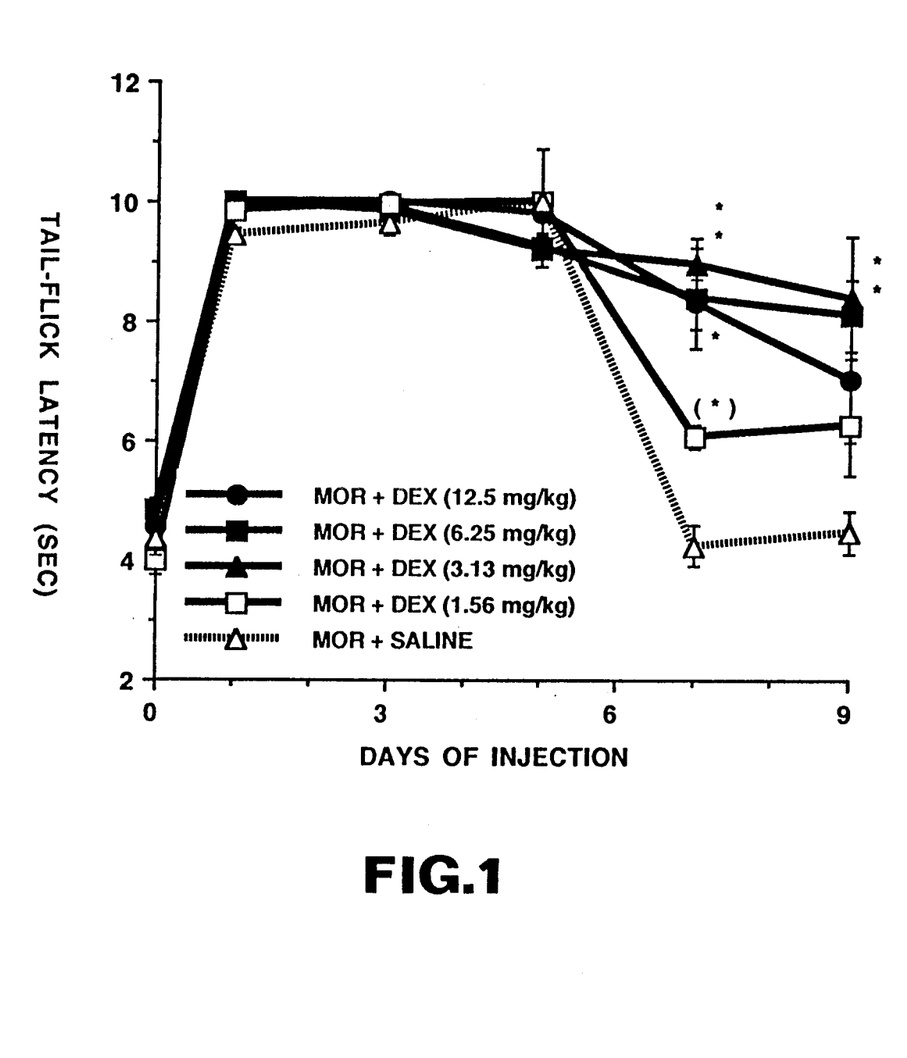
FIG. 1 shows the effects of systemic doses of dextrorphan (DEX) in inhibiting the development of tolerance to morphine analgesia in rats.

FIG. 1 shows the effects of systemic doses of dextrorphan (DEX) on tolerance to morphine analgesia produced by twice daily subcutaneous administration of 10 mg/kg morphine. Each symbol represents mean tail-flick latency scores (those above 4.5 seconds reflect analgesia) for each group of rats (N=5-6) and vertical bars are standard errors in this and the other figures. Baseline scores were between 4 and 5 seconds (at Day 0) and post-drug scores measured 1 hour after drug administration were close to 10 seconds for the first 5 days of daily drug administration. The control group (open triangles) show marked reduction in response to morphine (i.e., tolerance) at 7 and 9 days. In contrast, dextrorphan potently prevented the development of morphine tolerance as shown by no significant decreases in tail flick latencies, i.e., remaining analgesic during the whole course of repeated morphine administration. Asterisks indicate mean scores that were significantly different from those of the control group. All tested doses of dextrorphan were effective in preventing development of morphine tolerance with optimal doses ranging from 3.13 mg/kg to 12.5 mg/kg.

Figure 2:
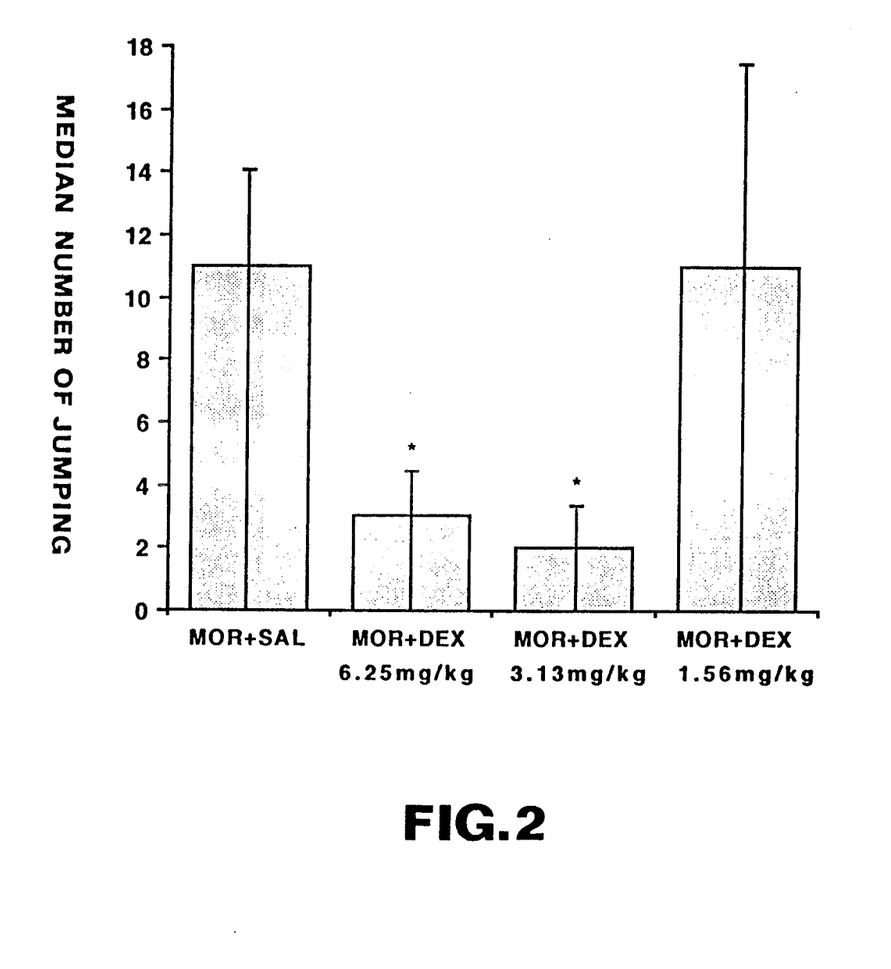
FIG. 2 shows the effects of systemic doses of dextrorphan on jumping, a withdrawal symptom produced by subcutaneous naloxone in rats previously injected with morphine.

FIG. 2 shows the effects of systemic doses of dextrorphan on jumping, a withdrawal symptom produced by subcutaneous naloxone (2 mg/kg) in rats previously injected with morphine (10 mg/kg) twice daily for 9 days. Asterisks indicate median number of jumps in dextrorphan treatment groups (MOR+DEX) that were significantly less than that of the control group (MOR+SAL). Vertical bars refer to the range of the numbers of jumps. Thus, 3.13 and 6.25 mg/kg dextrorphan (but not 1.56 mg/kg) significantly reduced the incidence of jumping in morphine tolerant rats, a behavioral manifestation of morphine dependence, brought about following subcutaneous injection with 2 mg/kg naloxone. Thus, coadministration of dextrorphan with morphine greatly inhibits the development of both tolerance to and dependence on morphine while the analgesic effect of the morphine remains substantially unaffected.

EXAMPLE 2

The effects of ganglioside $GM_1$ in inhibiting morphine tolerance and dependence utilizing both systemic and intrathecal treatment were evaluated. The systemic treatment procedure, including both morphine and ganglioside $GM_1$ administration, was exactly the same as that used in the experimental work presented in Example 1 except that ganglioside $GM_1$ was given 1 hour before each morphine administration.

Figure 3:
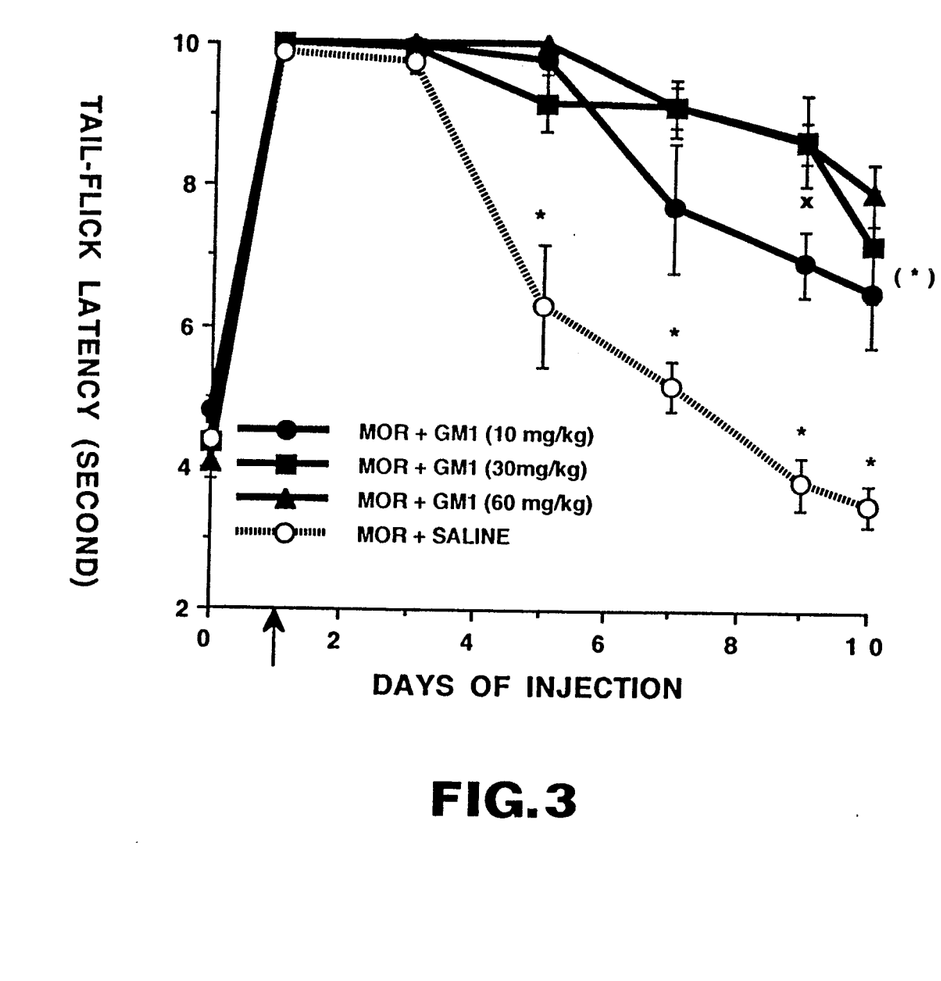
FIG. 3 shows the effect of ganglioside $GM_1$ in inhibiting the development of morphine tolerance in rats.

As shown in FIG. 3, the tail flick latency in ganglioside GM -treated (10, 30, 60 mg/kg, n=6/group) rats remained significantly longer than that of saline-treated rats on days 5, 7, 9 and 10 of repeated morphine administration, indicating the prevention of the development of morphine tolerance by ganglioside $GM_1$. Although all 3 doses of ganglioside $GM_1$ were effective, 30 and 60 mg/kg were more effective at days 9 and 10 than 10 mg/kg.

Figure 4:
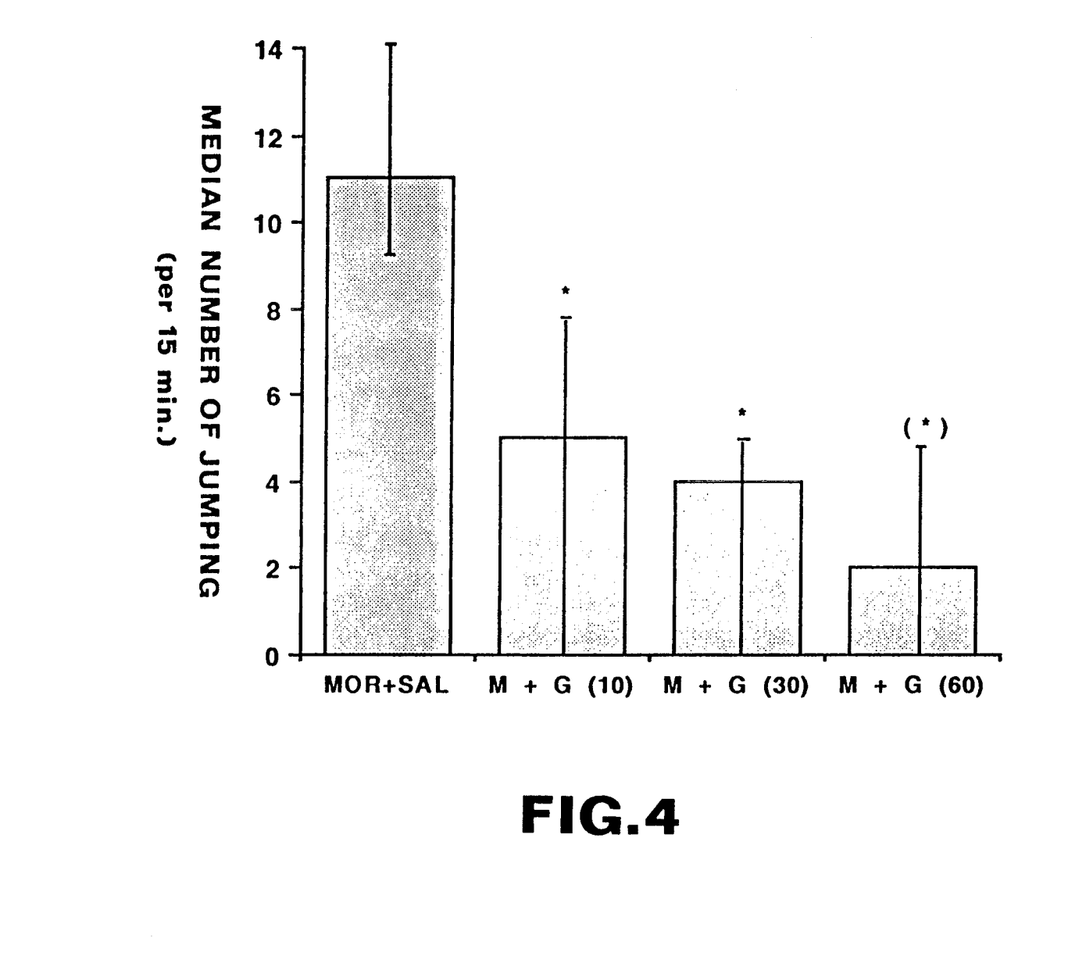
FIG. 4 shows the effects of systemic doses of ganglioside $GM_1$ on jumping rats.

FIG. 4 shows the effects of systemic doses of ganglioside $GM_1$ on jumping, a withdrawal symptom produced by subcutaneous naloxone (2 mg/kg) in rats previously injected with morphine (10 mg/kg) twice daily for 9 days. Asterisks indicate median number of jumps in $GM_1$ treatment groups (M+G) that were significantly less than that of the control group (MOR+SAL). Vertical bars refer to the range of the numbers of jumps. All three doses [10 mg/kg (10); 30 mg/kg (30); 60 mg/kg (60)] of GM were effective with 60 mg/kg $GM_1$ being the most effective dose tested.

EXAMPLE 3

This example demonstrates the effectiveness of ganglioside $GM_1$ in preventing the development of morphine tolerance at the site of the spinal cord. Morphine sulfate 10 μg was delivered once daily through an intrathecal (spinal) canula implanted 5 days before the first morphine injection. Ganglioside GM or saline also was delivered intrathecally 30 minutes before each morphine injection.

Figure 5:
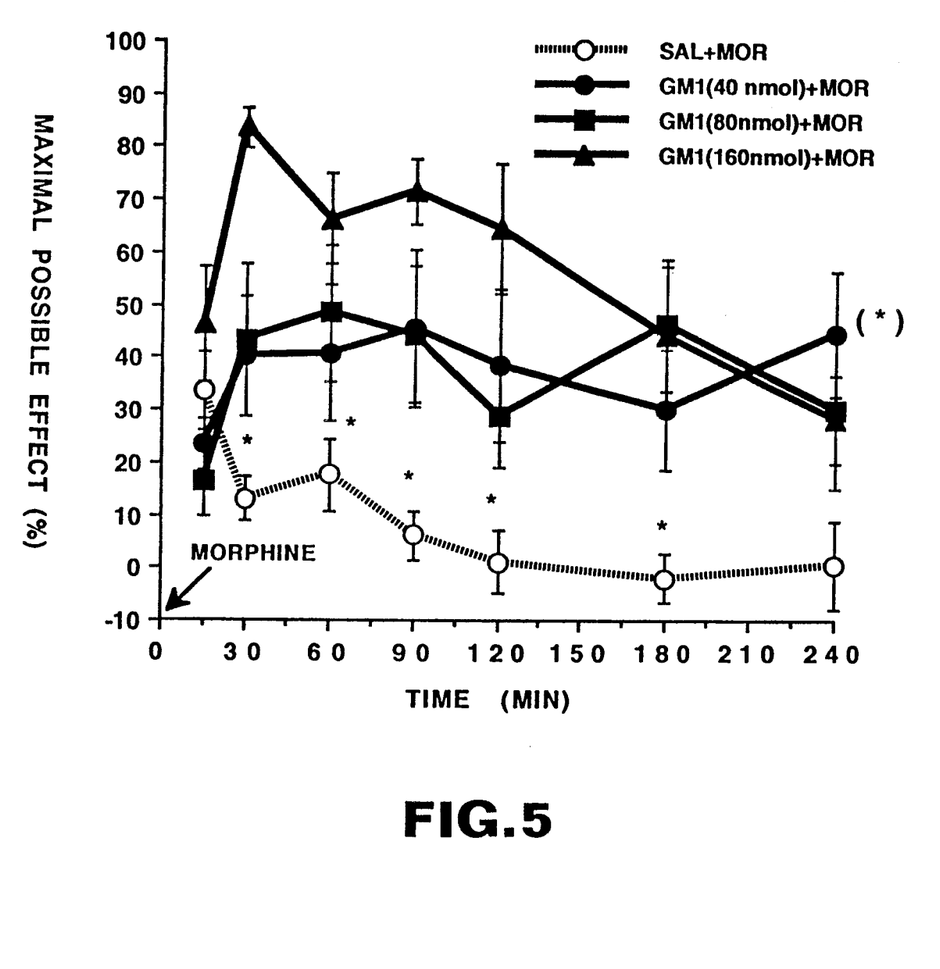
FIG. 5 shows the effects of intrathecal doses of ganglioside $GM_1$ on inhibiting the development of tolerance to morphine analgesia in rats.

FIG. 5 shows the effects of the intrathecal doses of ganglioside $GM_1$ on tolerance to morphine analgesia produced by once daily intrathecal administration of 10 μg morphine. Intrathecal ganglioside GM was given 30 min before each morphine administration. Each symbol represents mean scores for maximal possible effects (and hence analgesia) for each group of rats (n=5-6) measured at 15, 30, 60, 90, 120, 180, and 240 minutes after morphine injection on Day 8, i.e., 24 hours following 6 consecutive daily intrathecal morphine injections. Vertical bars are standard errors. Maximal possible effects (MPE) were calculated by the formula $\% MPE=[(TL-BL)/(10-BL)] \times 100$. TL: actual tail-flick latency; BL: baseline latency obtained before the first morphine injection; 10: cut-off time for radiant heat stimulation. The control group (open circle) showed marked reduction in response to morphine (i.e., tolerance) at each tested time point. In contrast, treatment with ganglioside GM$_1$ effectively prevented the development of morphine tolerance as indicated by significantly higher maximal possible analgesia effects of morphine (160 nmol>80=40 nmol) as compared to those of saline-treated rats. Asterisks indicate mean scores that were significantly different from those of other groups.

EXAMPLE 4

The effects of ganglioside GM$_1$ and the toxic NMDA receptor antagonist MK 801 on morphine tolerance were evaluated.

Figure 6:
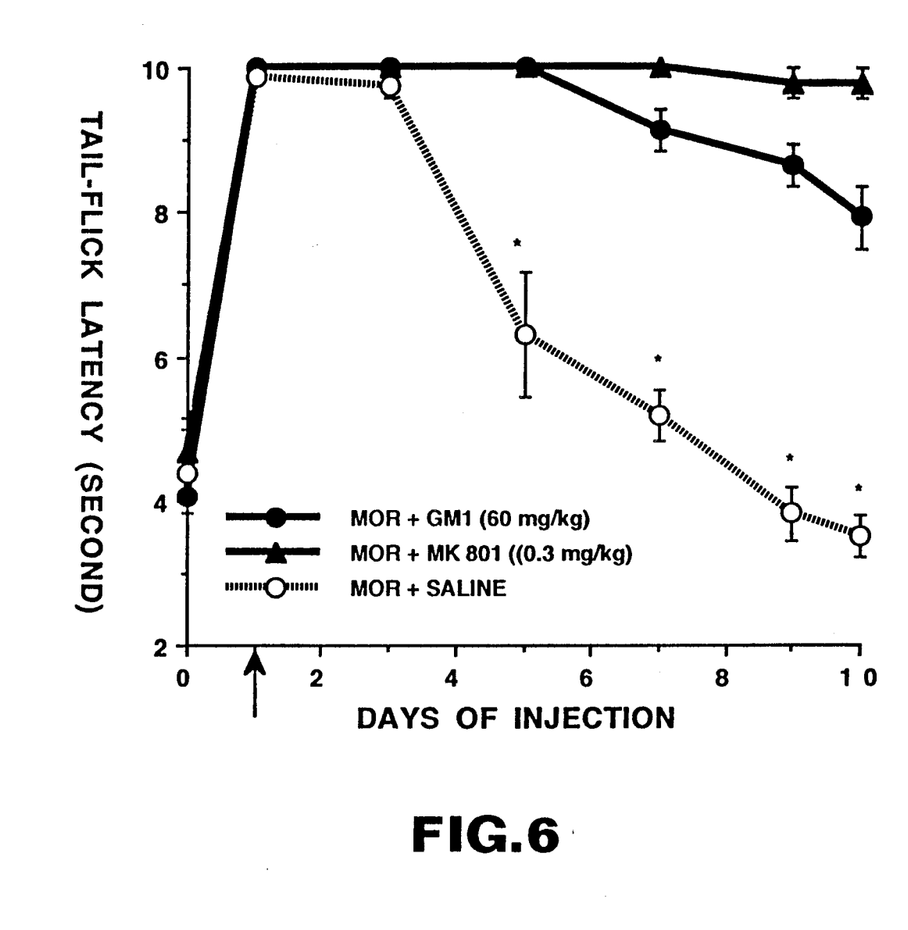
FIG. 6 shows the effects of ganglioside $GM_1$ in inhibiting the development of morphine tolerance to a degree which is equivalent to that of the neurologically toxic NMDA receptor antagonist MK-801.
Figure 7:
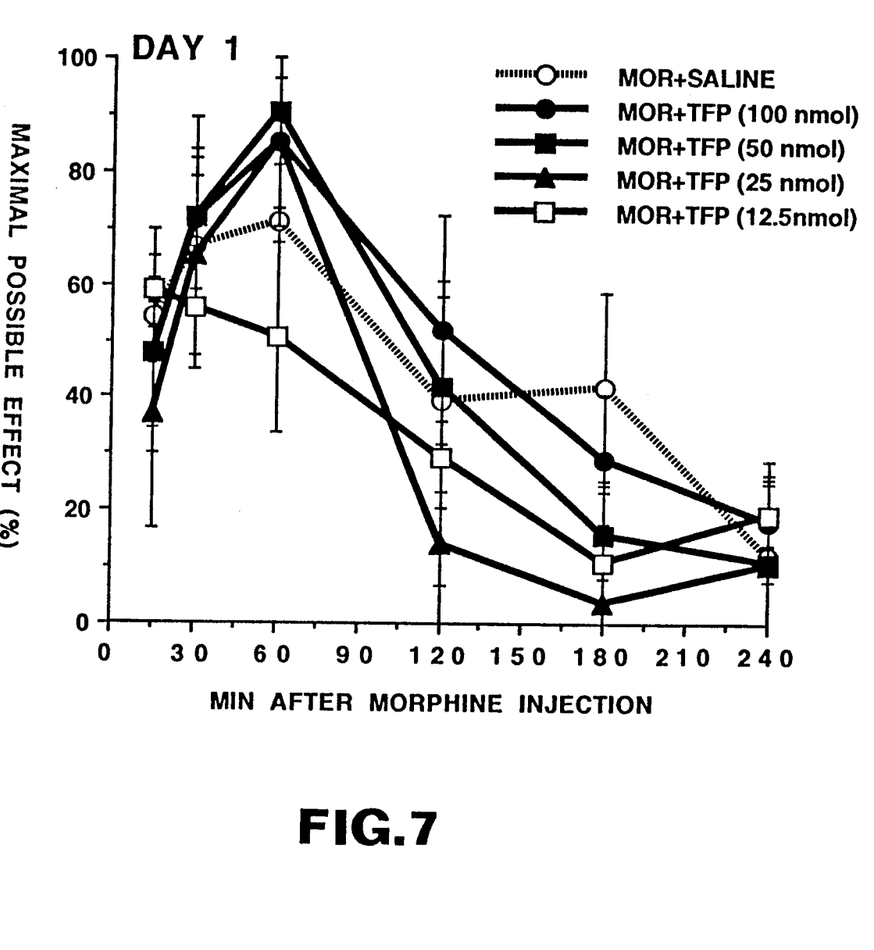
FIG. 7 and 8 show the effects of the calmodulin antagonist trifluoperazine (TFP) in inhibiting the development of morphine tolerance in rats; and, FIGS. 9 and 10 show the effects of the calmodulin antagonist N-(6-aminohexyl)-5-chloro-1-naphthalene sulfonamide hydrochloride (W-7) in inhibiting the development of morphine tolerance in rats.
Figure 8:
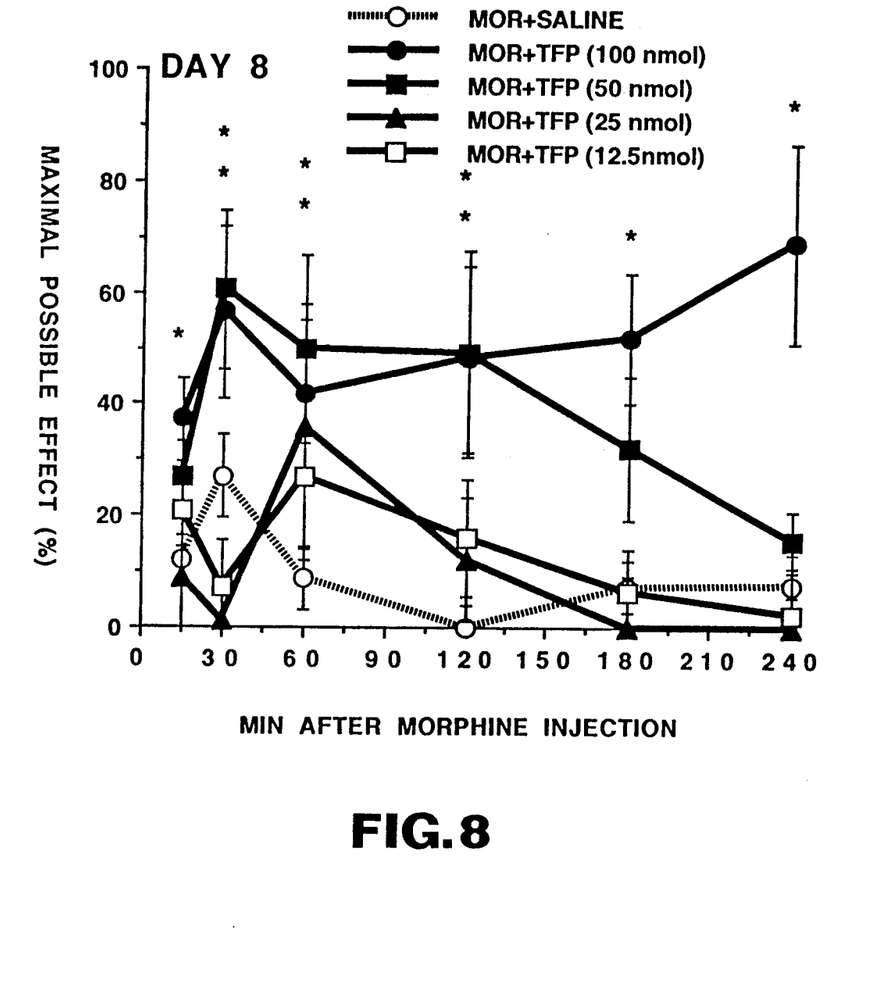
Figure 9:
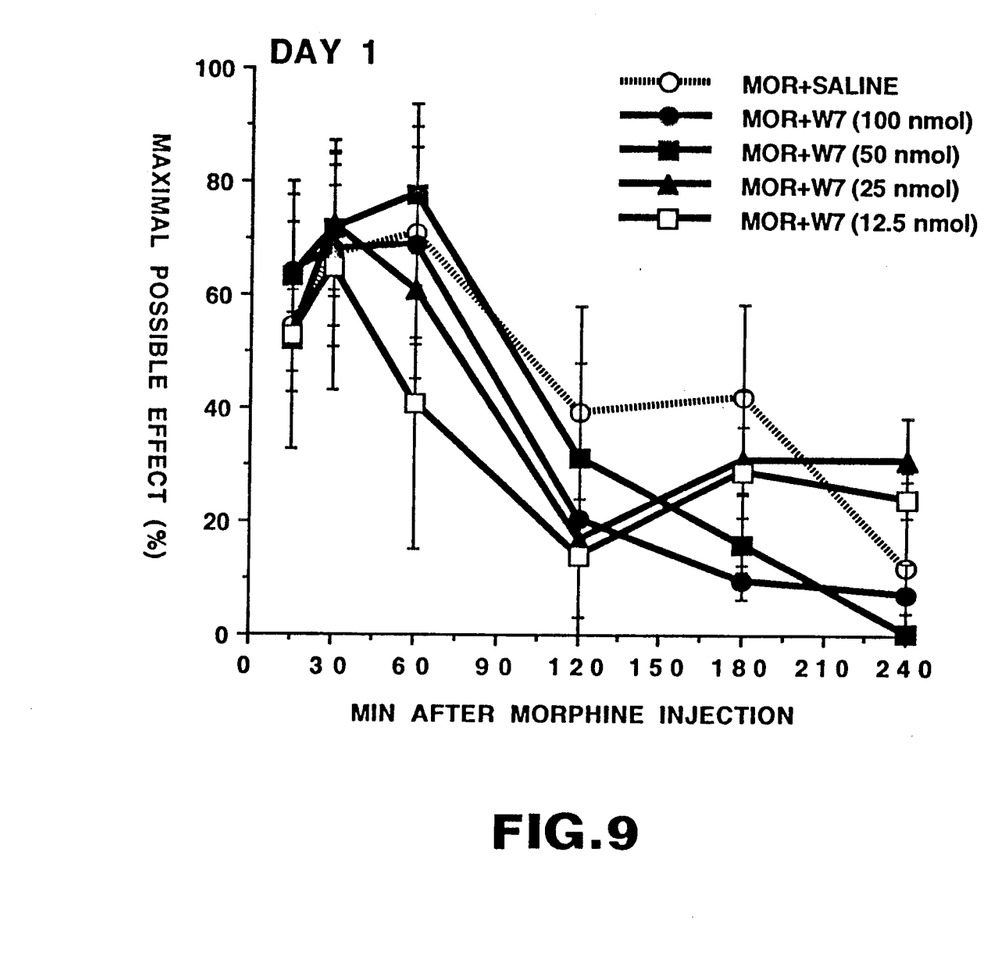
Figure 10:
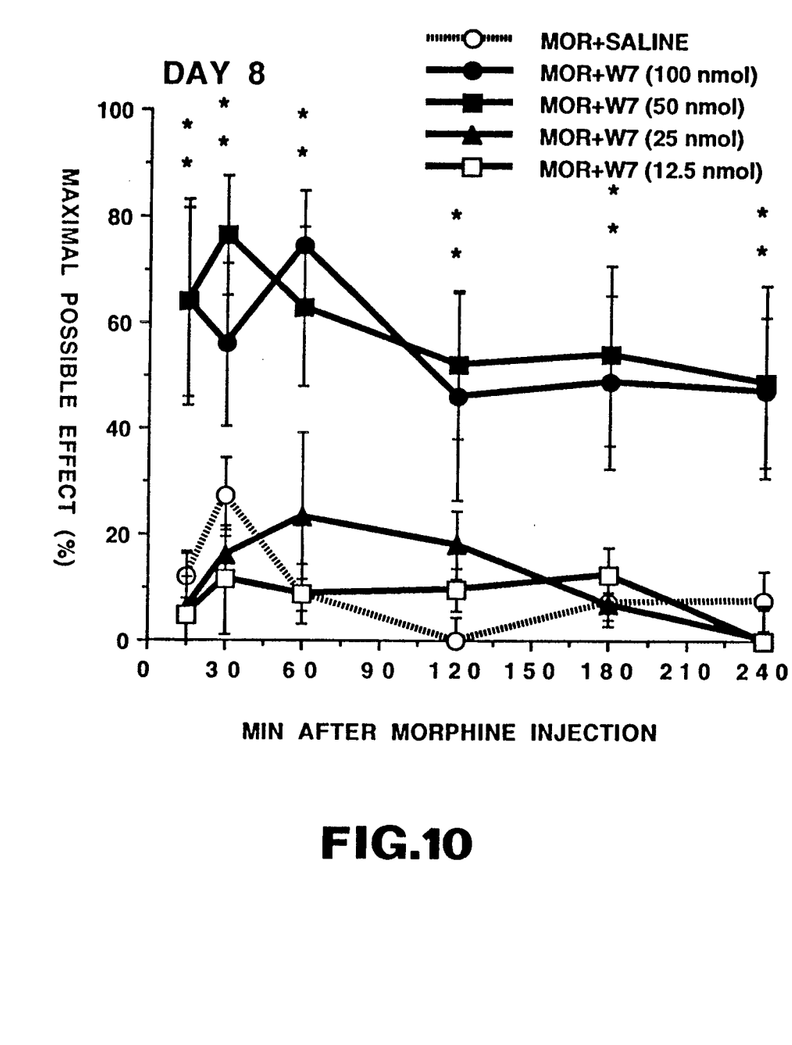

As shown in FIG. 6, treatment with ganglioside GM$_1$ (60 mg/kg) inhibited the development of morphine tolerance to the degree equivalent to that induced by 0.3 mg/kg MK 801. However, 50% (3 out of 6) of the rats treated with 0.3 mg/kg MK 801 died before the completion of the experiment and the remaining rats in the group showed apparently poor grooming and weight loss indicating adverse effects of MK 801 on health. The rats treated with ganglioside GM$_1$ or dextrorphan continued to appear well groomed and did not show weight loss. None of the rats in the GM$_1$ or dextrorphan treatment groups died due to drug administration. Thus, dextrorphan and GM$_1$ are nontoxic in contrast to MK 801 which exhibits severe cytotoxic effects and as such, is unlikely to be approved by the FDA for administration to humans.

EXAMPLES 5 AND 6

These examples illustrate the effects of the phenothiazine trifluoperazine (Example 5) and the naphthalenesulfonamide N-(6-aminohexyl)-5-chloro-1-naphthalenesulfonamide hydrochloride (Example 6) in preventing the development of morphine tolerance in rats.

Calmodulin is an intracellular cofactor necessary for the nitric oxide pathway that can be initiated upon NMDA receptor activation. FIGS. 7-10 demonstrate that trifluoperazine (TFP) and N-(6-aminohexyl)-5-chloro-1-naphthalenesulfonamide hydrochloride (W-7), both of which are calmodulin antagonists, effectively prevent the development of morphine tolerance in rats following intrathecal administration. In both cases, rats receiving once daily morphine sulfate (10 μg) and saline injection given intrathecally for 7 consecutive days developed tolerance to the analgesic effect of morphine as indicated by the reliable decrease in tail-flick latencies as compared to baseline latencies (day 1). In contrast, rats treated with TFP or W-7 (100 or 50 nmol) given immediately before each morphine administration showed a reliable analgesic effect of morphine (day 8) employing the same dose regimen used in the saline treatment group. The prevention of the development of morphine tolerance by TFP or W-7 is dose-related: 100=50 nmol>25=12.5 nmol. Each data point in FIGS. 7-10 represents the mean of a group of rats (n=6) and standard errors are shown by vertical lines. The asterisks refer to statistical differences ($\alpha=0.05$) between the saline group and each other group.

What is claimed is:

1. A composition comprising a narcotic analgesic and at least one nontoxic substance that inhibits the development of tolerance to and/or dependence on the narcotic analgesic, said nontoxic substance being selected from the group consisting of dextromethorphan, dextrorphan, trifluoperazine, N-(6-aminohexyl)-5-chloro-1-naphthalene sulfonamide, their mixtures and their pharmaceutically acceptable salts.

2. The composition of claim 1 wherein the narcotic analgesic is selected from the group consisting of alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine, their mixtures and their pharmaceutically acceptable salts thereof.

3. The composition of claim 1 in sustained release dosage form.

4. The composition of claim 1 wherein the nontoxic substance that inhibits the development of tolerance to and/or dependence on the narcotic analgesic is selected from the group consisting of dextromethorphan, dextrorphan, their mixtures and their pharmaceutically acceptable salts.

5. The composition of claim 4 wherein the narcotic analgesic is selected from the group consisting of codeine, fentanyl, heroin, hydrocodone, morphine, oxycodone, their mixtures and their pharmaceutically acceptable salts.

6. The composition of claim 5 wherein the narcotic analgesic is selected from the group consisting of codeine, fentanyl, heroin, hydrocodone, morphine, oxycodone, their mixtures and their pharmaceutically acceptable salts.

7. A method of inhibiting the development of tolerance to and/or dependence on a narcotic analgesic administered to a mammal which is liable to addiction thereto which comprises administering the narcotic analgesic to the mammal before, with or following administration to the mammal of a tolerance-reducing and/or dependence-reducing amount of at least one nontoxic substance that inhibits the development of tolerance to and/or dependence on the narcotic analgesic, said nontoxic substance being selected from the group consisting of dextromethorphan, dextrorphan, trifluoperazine, N-(6-aminohexyl)-5-chloro-1-naphthalene sulfonamide, their mixtures and their pharmaceutically acceptable salts.

8. The method of claim 7 wherein the narcotic analgesic is selected from the group consisting of alfentanyl, alphaprodine, anileridine, bezitramide, codeine, dihydrocodeine, diphenoxylate, ethylmorphine, fentanyl, heroin, hydrocodone, hydromorphone, isomethadone, levomethorphan, levorphanol, metazocine, methadone, metopon, morphine, opium extracts, opium fluid extracts, powdered opium, granulated opium, raw opium, tincture of opium, oxycodone, oxymorphone, pethidine, phenazocine, piminodine, racemethorphan, racemorphan, thebaine, their mixtures and their pharmaceutically acceptable salts thereof.

9. The method of claim 7 wherein the nontoxic substance that inhibits the development of tolerance to and/or dependence on the narcotic analgesic is selected from the group consisting of dextromethorphan, dextrorphan, their mixtures and their pharmaceutically acceptable salts.

* * * * *